United States Patent
Magal (10) Patent No.: US 8,636,201 B2
(45) Date of Patent: Jan. 28, 2014

(54) AUTOMATIC IDENTIFICATION SYSTEM FOR RANDOMLY ORIENTED OBJECTS

(76) Inventor: Eliezer Magal, Udim (IL)

( * ) Notice: Subject to any disclaimer, the term of this patent is extended or adjusted under 35 U.S.C. 154(b) by 214 days.

(21) Appl. No.: 13/063,759

(22) PCT Filed: Sep. 14, 2009

(86) PCT No.: PCT/IL2009/000896
§ 371 (c)(1),
(2), (4) Date: Mar. 14, 2011

(87) PCT Pub. No.: WO2010/029558
PCT Pub. Date: Mar. 18, 2010

(65) Prior Publication Data
US 2011/0168774 A1    Jul. 14, 2011

Related U.S. Application Data
(60) Provisional application No. 61/096,843, filed on Sep. 14, 2008.

(51) Int. Cl.
*G06F 17/00* (2006.01)
(52) U.S. Cl.
USPC .......................... 235/375; 235/380; 235/383
(58) Field of Classification Search
USPC .................. 235/383, 487, 494, 380, 375, 407
See application file for complete search history.

(56) References Cited

U.S. PATENT DOCUMENTS

| | | | |
|---|---|---|---|
| 6,256,404 B1 * | 7/2001 | Gordon et al. | 382/131 |
| 6,419,680 B1 | 7/2002 | Cosman et al. | |
| 7,164,360 B2 * | 1/2007 | Schiebler | 340/572.9 |
| 8,020,768 B2 * | 9/2011 | Ramos-Elizondo et al. | 235/385 |

FOREIGN PATENT DOCUMENTS

| | | |
|---|---|---|
| GB | 983950 | 2/1965 |
| GB | 2062917 | 5/1981 |
| WO | WO 83/00760 | 3/1983 |
| WO | WO 2010/029558 | 3/2010 |

OTHER PUBLICATIONS

International Preliminary Report on Patentability Dated Mar. 24, 2011 From the International Bureau of WIPO Re.: Application No. PCT/IL2009/00896.
International Search Report and the Written Opinion Dated Jan. 25, 2010 From the International Searching Authority Re.: Application No. PCT/IL2009/000896.
Communication Pursuant to Article 94(3) EPC Dated Mar. 18, 2013 From the European Patent Office Re. Application No. 09748152.7.

* cited by examiner

*Primary Examiner* — Karl D Frech (57) ABSTRACT

A method of identifying a plurality of items, the method comprising: performing a CT scan of a plurality of items, at least some of said items bearing information tags; reconstructing an image based on the CT scan; and identifying an information tag associated with the items based on the reconstructed image.

55 Claims, 5 Drawing Sheets

AUTOMATIC IDENTIFICATION SYSTEM FOR RANDOMLY ORIENTED OBJECTS

RELATED APPLICATIONS

This application is a National Phase of PCT Patent Application No. PCT/IL2009/000896 having International filing date of Sep. 14, 2009, which claims the benefit of priority of U.S. Provisional Patent Application No. 61/096,843 filed on Sep. 14, 2008. The content of the above applications are all herein by reference.

The content of the above document is incorporated by reference as if fully set forth herein.

FIELD AND BACKGROUND OF THE INVENTION

The present invention, in some embodiments thereof, relates to a method and system for identifying unorganized items, more particularly, but not exclusively, to identifying unorganized items with Computerized Tomography (CT).

The term "unorganized items" as used herein refers to a number of different items placed or piled in an unorganized way such that part of the items can be covered or hidden one by the other. The different items may have different sizes, shapes and/or be made of different materials. The items may also cause passive or active electromagnetic interference for example they may comprise metal or aluminum that block electromagnetic or RF signals.

In the art, the identification of such unorganized items required treating each item independently, for example by scanning a barcode or UPC (Universal Product Code) on the item's package. This usually also requires organization of the items in order to expose the barcode on the package.

Another method known in the art is the use of RFID tags on the items. While an RFID reader has the ability of scanning a plurality of items at once, the scanner may be blocked by presence of metal or any other electromagnetically active or passive interferer in the items. In addition, RFID tags are relatively expensive and therefore not adapted for wide scale use, especially for low value items.

CT is used in various fields. An object is irradiated (by X-rays, gamma rays or other radiation) and attenuation data is acquired from different directions. A set of 2-D images or a 3-D image of the object is reconstructed showing the internal structure of the object such as density distribution, dimensions and shape.

CT is common in medical applications where the scanned objects are human patients, and in security applications for scans of luggage. CT is sometimes also used in other fields such as industrial or academic use, for example for evaluating properties of materials or for studying biological and paleontological specimens.

SUMMARY OF THE INVENTION

An aspect of some embodiments of the invention relates to the identification of unorganized items by use of CT scanning. In some embodiments of the invention, at least some of the items comprise an information tag according to which information regarding the items is identified. Preferably, the image reconstructed from the CT scan shows the information tags of the items.

In accordance with an embodiment of the invention there is provided a method of identifying a plurality of items, the method comprising:

performing a CT scan of a plurality of items, at least some of said items bearing information tags;

reconstructing an image based on the CT scan; and identifying an information tag associated with the items based on the reconstructed image.

In some embodiments, identifying the tag comprises identifying a unique material on the tags. In some embodiments, identifying an information tag comprises identifying a plurality of materials, where a tag may comprise different materials and where different tags may comprise different sets of materials. In some embodiments, identifying an information tag comprises identifying bits of high attenuation material on or in the tags. In some embodiments, identifying an information tags comprises identifying a predefined geometrical shape of the tags. In some embodiments, identifying an information tag comprises identifying a pattern on the tag. In some embodiment, identifying an information tag comprises identifying by a shape or pattern recognition algorithm. In some embodiments, identifying an information tag comprises identifying a combination of any of materials and geometrical shapes of the tag.

In some embodiments, the method further comprises reading information related to the item from the information tag. In some embodiments, reading information comprises reading a pattern embedded in the tag. In some embodiments, reading information comprises identifying bits embedded in the tags. In some embodiments, reading information comprises identifying grooves or holes in the tag. In some embodiments, identifying grooves or holes comprises identifying a CT number of a material filling the grooves or holes.

In some embodiments, the method further comprises:
analyzing the shape and CT number of an item; and
comparing said shape and/or CT number with the information read from the tag.

In some embodiments, the method further comprises:
generating a warning when said comparison is negative.

In some embodiments, identifying an information tag based on the reconstructed image comprises:
identifying a plane on which the information tag is positioned based on the reconstructed image;
reconstructing a 2-D image of the plane on which the tag is identified; and
identifying the tag based on the 2-D image.

In some embodiments, identifying an information tag based on the reconstructed image comprises reading information from the information tag from the 3D image. In some embodiments, reading information from the information tag comprises analyzing only voxels in the image where information is expected to be located.

In some embodiments, constructing an image based on the CT scan comprises constructing a first low resolution image of said items and constructing a second higher resolution image of the volume around the located tags.

In some embodiments, the method further comprises providing an item holder containing said plurality of items. In some embodiments, providing an item holder comprises providing an item holder containing a plurality of information tags associated with the plurality of items and wherein performing a CT scan of a plurality of items comprises performing a CT scan of the plurality of tags. In some embodiments, providing an item holder containing a plurality of information tags comprises providing an item holder containing a plurality of information tags wherein at least one of the tags is associated with an item that is not in the item holder. In some embodiments, providing an item holder containing a plurality of information tags comprises providing an item holder containing a plurality of information tags wherein at least one of the tags is not associated with a particular item. In some embodiments, providing an item holder comprises providing an item holder made of a low attenuation coefficient material.

In some embodiments, the method further comprises:
generating information on the items associated with the tags.

In some embodiments, the method further comprises:
analyzing the outer surface or the CT number of an item from the plurality of items; and
checking if information on said item is provided in the generated information.

In some embodiments, constructing an image based on the CT scan, further comprises one or more of noise filtering, edge enhancement, segmentation (division to sub volumes of different densities), pattern recognition, multi-planar reconstruction and curved multi-planar reconstruction.

In some embodiments, the method further comprises:
detecting that the reconstructed image is noisy and
performing an additional CT scan of the items.

In some embodiments, the method further comprises:
detecting that the signals detected by the CT scan are low; and
performing an additional CT scan of the items.

In some embodiments, performing an additional scan comprises performing an additional scan with different scan parameters than the first CT scan.

In some embodiments, the method further comprises:
calculating a total volume of the items from the reconstructed image;
comparing said calculated volume with the expected volume based on information read from the information tags.

In some embodiments, calculating a total volume of the items comprises calculating a total volume of a specific CT number in the items.

In some embodiments, the method further comprises:
generating a warning if any of the items generates image artifacts or if the tags might be tampered with.

In accordance with an embodiment of the invention there is provided an information tag for providing information on items, the tag comprising:
a body made of one or more materials and comprising a marking for orienting the tag in a 3D image; and
incisions or holes in the body coding item information.

In some embodiments, said marking is an engraving in the body. In some embodiments, said marking is an asymmetric shape of the body. In some embodiments, said marking is a predefined material embedded in the tag.

In some embodiments, the one or more materials have a different radiation attenuation coefficient than the item which the tag is associated with. In some embodiments, the body has a predefined geometrical shape, adapted to be identified in a CT image.

In some embodiments, the incisions or holes represent information of a bar code. In some embodiments, the body comprises a template of holes and wherein the incision or holes are holes punched in said template. In some embodiments, the incisions or holes comprise different shapes. In some embodiments, the incisions or holes are filled with a different material than the materials of the body. In some embodiments, different holes are filled with different materials.

In accordance with an embodiment of the invention there is provided a system for identifying a plurality of items, the system comprising:
a CT scanner operable to scan a plurality of items, the items comprising one or more tags including information for said items;
an image reconstructor adapted to reconstruct an image of said items; and
a controller adapted to locate the tags within said image and read the information on the tags from said image.

In some embodiments, the controller is further adapted to generate a warning when an item of the plurality of items interferes with the CT scan. In some embodiments, the controller is further adapted to instruct rescanning of the items with different parameters when low signals are detected during the scan. In some embodiments, the controller is further adapted to instruct rescanning of the items with different parameters when the quality of the reconstructed image is insufficient for locating the tags.

In some embodiments, the controller is further adapted to compare the volume of the items in the reconstructed image with an expected volume of the items as derived from the information on the tags. In some embodiments, the compared volume is a volume of a specific CT number in the reconstructed image. In some embodiments, the controller is further adapted to generate a warning when the expected volume of the different materials is different than the volume derived from the information on the tags.

In some embodiments, the CT scan is operable to scan tags without their associated items.

In some embodiments, the system further includes a scale for weighing the items and the controller is further adapted to compare the weight of the items with an expected weight of the items as derived from the information on the tags.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In some embodiments of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to a method and system for identifying unorganized items, more particularly, but not exclusively, to identifying unorganized items with Computerized Tomography (CT).

In some embodiments of the invention the items are placed in an item holder which passes a CT scan. A 3-D image of the items is optionally reconstructed from the CT scan. The items are then identified based on the reconstructed image. Optionally, the image shows information tags located on the items and information on the items is obtained by identifying the information tags.

The item holder may be any holder in which the items are kept, such as for example a box, bag or shopping cart, or an item holder specifically designed for the CT scan system. Preferably, the item holder is made of material of relatively low attenuation for the radiation used by the CT, such that the item holder does not introduce artifacts in the CT image of the items.

It is noted that in accordance with some embodiments of the invention, no manual interaction is required in order to identify the items in the item holder and the identification is done automatically. The item holder may be driven by a conveyer belt or other driving means through the CT scan and a controller may be used for identifying and/or listing the items. Moreover, the items may be identified while placed in a closed or sealed item holder, without requiring opening thereof. In some embodiments, a plurality of items in an item holder may be identified in a single CT scan.

Optionally, the identification of the items involves some manual interaction.

In some embodiments of the invention, the controller provides information on the items in the item holder. The provided information may include various information about the items, such as for example product ID, price, type, manufacturer, manufacturing or expiry date, price, weight, material, serial number, etc.

An aspect of some embodiments of the invention refers to information tags for the items. The tags include information about the items and/or an identification code, such as are described below, by which the items can be identified and/or information which is not directly associated with an item, such as special discounts etc. In some embodiments of the invention, at least some of the items comprise an information tag according to which the items can be identified. In some embodiments of the invention, items to be identified are each provided with an information tag. Optionally, some information tags are inserted into an item holder without their associated item. Optionally, some items comprise more than one information tag. Optionally, information tags are inserted in the item holder without being associated with a particular item, such as for example an information tag identifying a buyer of the items.

In various of the exemplary embodiments of the invention, the information tag is adapted to be imaged in a CT scan. According to some embodiments of the invention, the tag may be identified by one or both of identifying a geometrical shape or a material of or in the tag. A geometrical shape of a tag, as referred herein includes a geometrical outer surface of a tag and/or a pattern embedded in the tag. A material of the tag, as referred herein, may be one or more materials of which the tag is made or a material which is only part of the tag.

In some embodiments of the invention, the tag comprises or is made in a predefined geometrical shape which is not expected to be present in the items or item holder. The predefined shape may be an external contour of the tag or a marking in the tag, for example, one or more holes, engravings or protrusions on the tag. Optionally, the marking in the tag and/or the external contour is used for orientation of the tag in a 3D image.

In some embodiments of the invention, different tags associated with different information have different geometrical shapes. Optionally, the different geometrical shapes are all shapes which are not expected to be present in the items or item holder.

In some embodiments of the invention, the tag, having a predefined geometrical shape, is made from a material whose radiation attenuation characteristics different from the item to which it is attached or associated with. The different attenuation characteristic assists in imaging the tag and differentiating it from the item it is attached to or embedded in. Optionally, different tags, for example, for different items, are made from different materials.

In some embodiments of the invention, the attenuation coefficients of the materials of the tags are known by the controller and assist in identifying the tags in the reconstructed image.

In some embodiments of the invention, an information tag is made from a unique material. A unique material as referred to herein comprises a material whose attenuation coefficient is not expected to be present in any of the items or in the item holder. According to this embodiment, the tag may be identified by identifying its material only, for example by windowing the reconstructed image according to the unique material. Optionally, the tag is not made from a unique material but only comprises sufficient unique material for imaging and optionally orienting the tag. For example, the tag may include three dots or bits of unique material which are enough to identify a plane on which the tag is positioned.

In some embodiments of the invention, the tag has a 3D shape which includes a thickness of at least 0.1 mm. Optionally, the thickness of the tag is at least 0.2 mm or 0.5 mm.

Optionally, the tag has a thickness of about 1, 2, 3 or 5 mm. The depth of the tag assists in locating the tags in the reconstructed CT image.

In some embodiments of the invention, the tag carries information on the item it is associated with. Optionally, the item information provided on the tag also has a thickness. In some embodiments of the invention, the item information on the tag is marked by non-continuous surface of the tag. For example, by channels, engravings, holes or protrusions on the surface of the tag. In some embodiments the channels, engravings or holes are filled with different materials from a base material of the tag, or the protrusions are made from different materials, In some exemplary embodiments of the invention, the tag carries information encoded as a pattern. Optionally, the information on the tag encodes information of a barcode of the item it is associated with. Optionally, the tag encodes information which is not directly related to an item. Optionally, the encoding on the tag is a pattern of holes or engravings. Optionally, the information carried by the tag also assists in identifying the tag in the reconstructed image.

In some embodiments of the invention using information tags, the tags are made from a material with a limited radiation attenuation coefficient. This is advantageous since the tag does not completely block the radiation used for the CT scan and does not introduce image artifacts in the CT image.

Once the volume of the item holder is scanned and the image is reconstructed, the image is analyzed using image processing methods known in the art. First, the location and/or orientation of the tag or tags within the volume are determined. Then, a closer and optionally a higher resolution view of the tag environment is analyzed in order to read the identification code or information on the tag. Optionally, the information is encoded as a 2-D pattern of holes, grooves or other features identifiable in the image. A 2-D image of the plane of the tag is reconstructed using any of the techniques known in the art as multi-planar reformatting or slab display in order to read the information on the tag. In some embodiments, the 3-D image is reconstructed at a relatively low resolution and a higher resolution image is then reconstructed at the identified locations or planes for reading of the tag information.

However, since the tag may be bent (as, for example, around a cylindrical surface) and be located on more than one plane, in accordance with some embodiments of the invention, the information on the tag is read from the 3-D image or from an image known in the art as curved multi-planar reformatted. In some embodiments, the item information carried by the tag may be in a 3D form, for example by engravings or holes having different depths or on different sides or surfaces, in such cases, the information on the tag will be read from a 3D-image. In any event, the tag can be identified and the information can be read from the 3-D image (as described below) for flat tags having two dimensional patterns as well as for shaped tags.

The tag may be attached, embedded, affixed, tied, or can be part of the item or the item's package.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
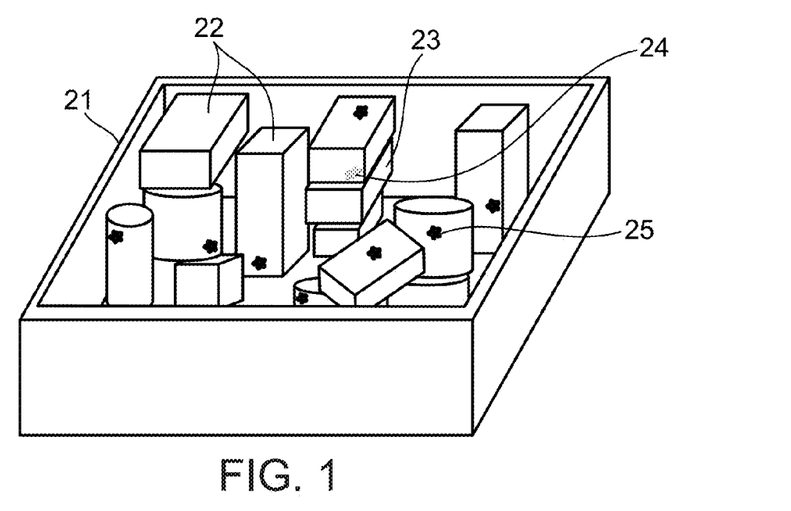
FIG. 1 is a schematic illustration of an item holder including a plurality of unorganized items in accordance with some embodiments of the invention.
Figure 2A:
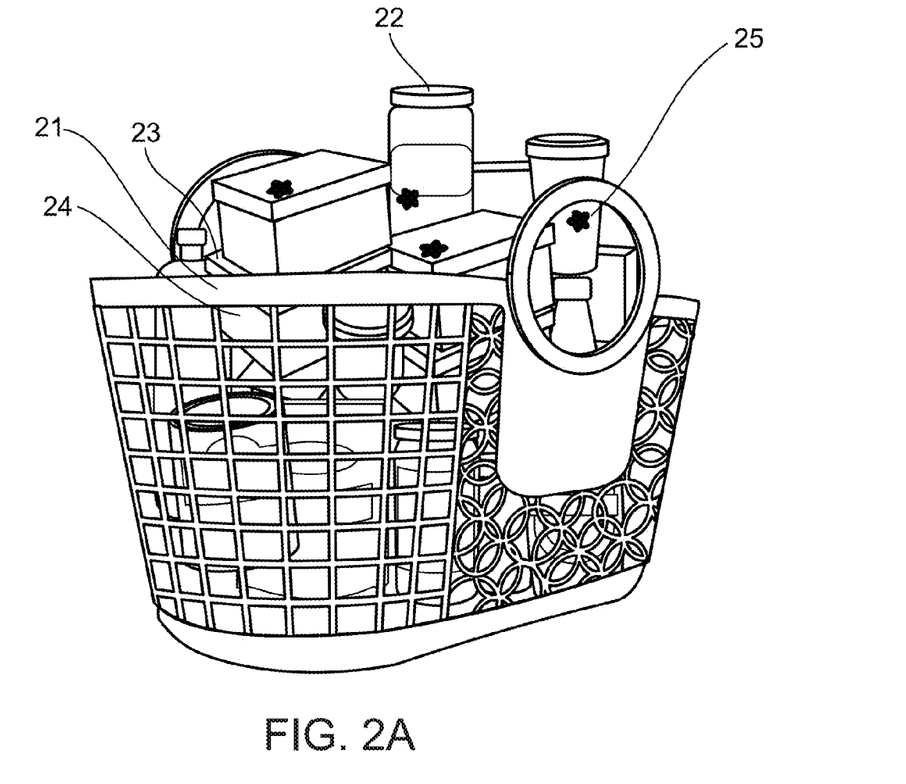
FIG. 2A is a schematic illustration of an item holder including a plurality of unorganized items in accordance with another exemplary embodiment of the invention.
Figure 2B:
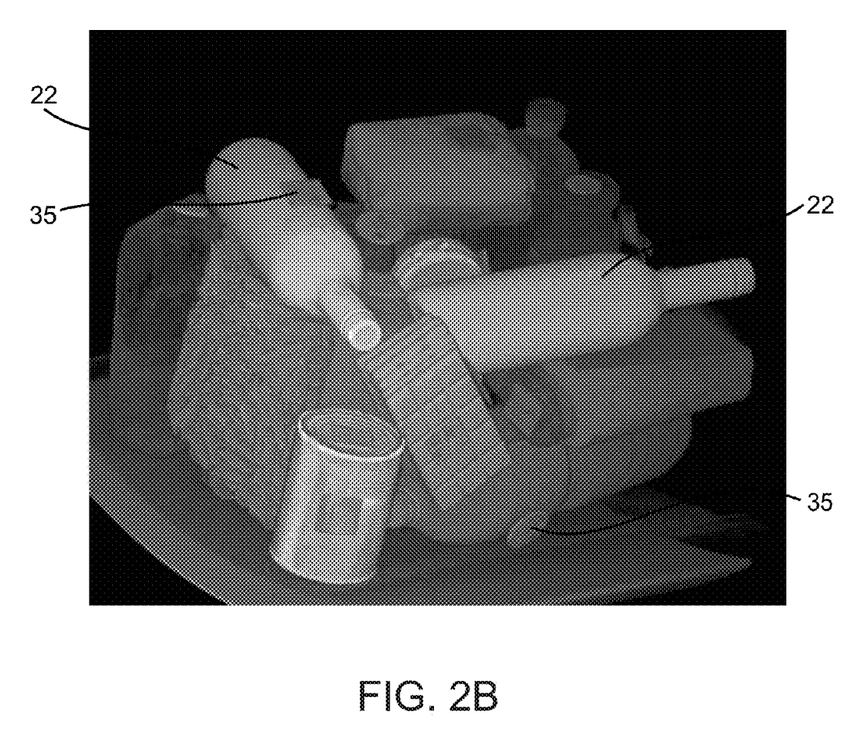
FIG. 2B is an illustration of a CT reconstructed image of an item holder in accordance with some embodiments of the invention.

Referring now to the drawings, FIGS. 1 and 2 illustrate an item holder 21 including a plurality of unorganized items 22 in accordance with exemplary embodiments of the invention.

An item holder according to some embodiments of the invention may include 5, 10, 20, 50, 100, 1000 items or more. At least some of items 22 optionally comprise an information tag 25. Optionally, an item may comprise more than one tag, for example when the item is a package including a number of products or when a special discount is given to an item, the item will have a tag for its regular price and a tag identifying the discount. Optionally, a tag may be inserted in the item holder without having an associated item, for example for identifying the owner of the item holder.

Figure 4:
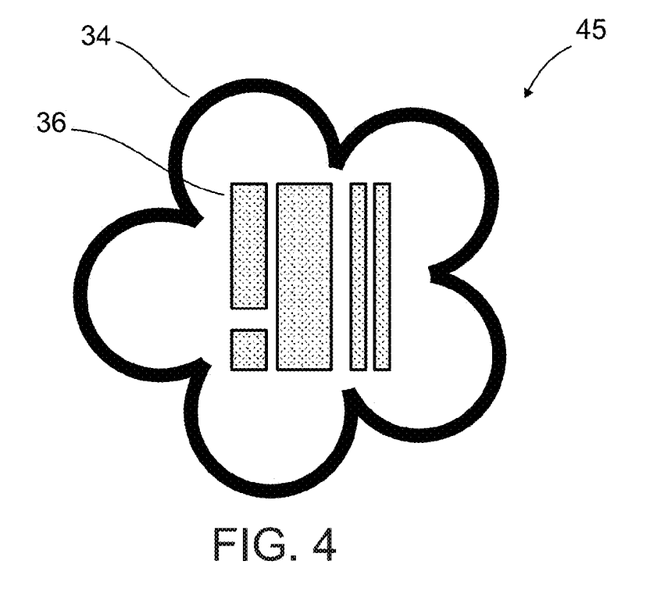
FIG. 4 is a schematic illustration of an information tag in accordance with some embodiments of the invention.
Figure 5A:
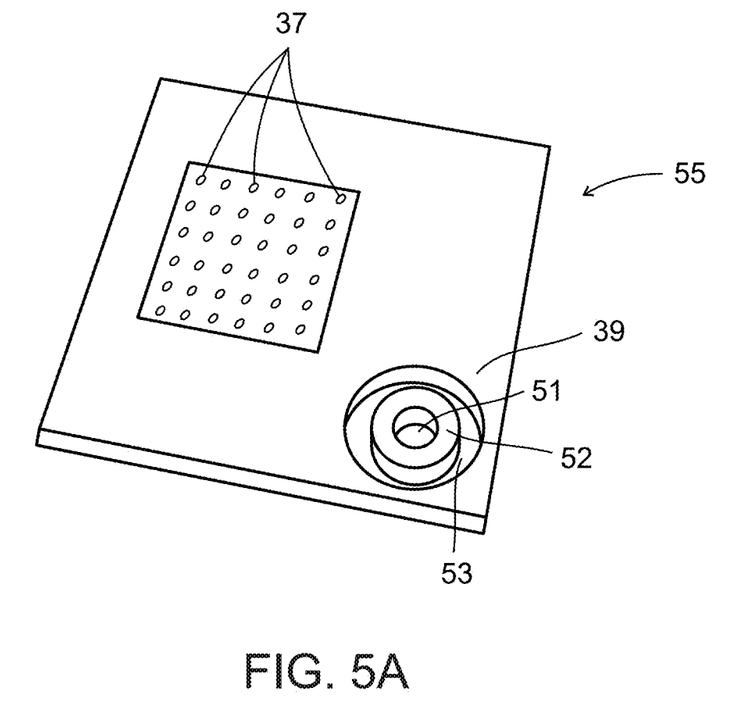
FIGS. 5A and 5B are schematic illustrations of other information tags in accordance with other exemplary embodiments of the invention.
Figure 5B:
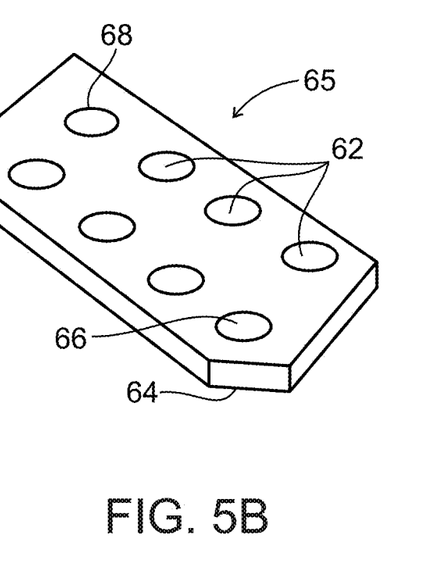

Information tags 25 are depicted in FIGS. 1 and 2 as flower shaped stickers, however, any suitable information tag of any suitable identifiable shape and/or material, such as those detailed with respect to FIGS. 4 and 5, can be used.

The items are optionally positioned in an unorganized way inside item holder 21 and some items may be piled one on the other or leaning at an angle with respect to others. For example, an item 23 is covered by another item such that its tag 24 is visually hidden. The items can be covered partially, or an entire surface of an item may be covered by one or more other items. A number of items can also be attached to each other or even packed together inside item holder 21. For example inside a sealed package, a plastic bag or attached by a rubber band. Some of the items may be oriented so that the tags on different items are not in the same or perpendicular planes. In addition, the items may not have flat surfaces, and a tag on the item may be non-planar.

Item holder 21 may have a form of a rectangular box as illustrated in FIG. 1 or be a grocery bag as illustrated in FIG. 2. In accordance with other embodiments of the invention, item holder 21 can be made of any material and can have any shape. Preferably the material of the item holder does not interfere with the CT scan. For example, item holder 21 may be a bag, basket, luggage of various shapes or an item holder specifically designed for the CT scan system. Optionally, item holder 21 is sealed such that the items are not visible to the human eye. This can be useful for example when verifying the contents of a package that was ordered and is to be delivered.

Items 22 may be any item positioned in an item holder. For example, in the embodiment illustrated in FIG. 2A, items 22 are grocery items.

Figure 3:
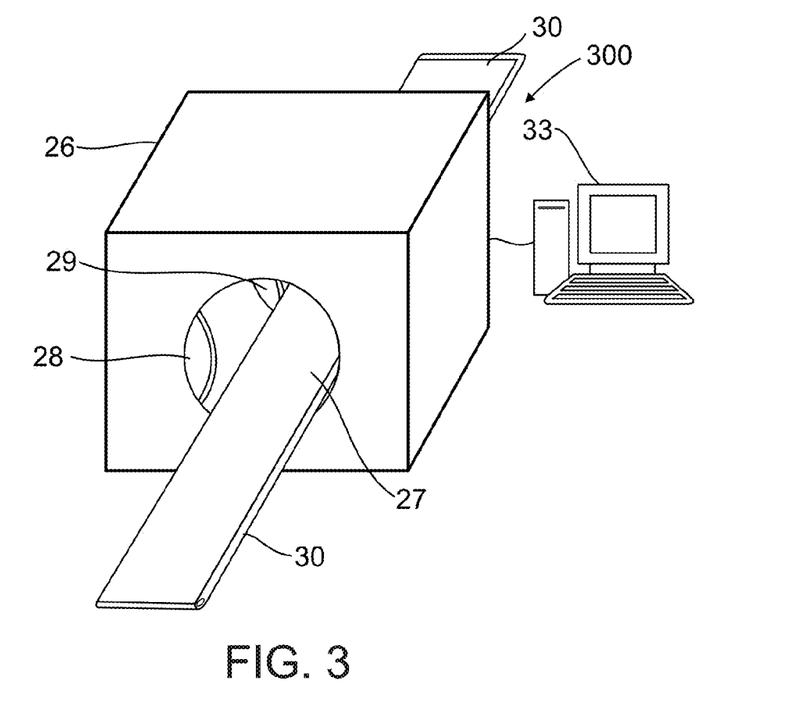
FIG. 3 is a schematic illustration of a CT scan system and controller in accordance with some embodiments of the invention.

FIG. 3 is a schematic illustration of a CT scanner system 300 in accordance with some embodiments of the invention. System 300 includes a CT scanner 26 having a scanning volume 27 into which an item holder can be inserted. The scan volume 27 is large enough to contain a cross section of item holder 21. Optionally, some of the items are kept outside the item holder while their associated tags are inserted in the item holder. Items which are not inserted in the item holder can be for example items which are too large for insertion in item holder 21, items made of material not suitable for a CT scan, items which are radiation sensitive or items that are not available at the time and location of the scan.

CT 26 optionally comprises a conveyer belt 30 for driving the item holders through the CT. Alternatively, other driving means are used to load the item holder into the scan volume. CT scan can also comprise an entrance door 28 and an exit door 29 which are preferably closed during the scan operation. Alternatively the CT unit can have hanging x-ray blocking strips, as are generally found in X-ray scanners on airports. The entrance door opens for entry of an item holder and closes before starting the CT scan. The exit door will open after the scan operation for evacuating the item holder from volume 27. Optionally the item holder is loaded and unloaded through the same port. The system is optionally provided with one or two tunnels (not shown in FIG. 3) through which the item holder is loaded and unloaded. Such tunnels may be useful for improved radiation shielding.

In some exemplary embodiments CT scanner 26 is an X ray CT scanner. The scanner comprises a gantry with a rotating frame carrying at least one X-ray source (not shown). The X-ray source is operable to irradiate the item holder from multiple directions. In some embodiments the source irradiates the items from 360° or more. In some embodiments the source irradiates the items from at least 180°.

The CT scanner can be a scanner operating on any of the well known conventional principles. In some embodiments, a detector (not shown) is positioned opposite the radiation source and is operable to measure the radiation attenuated by the items. In some embodiments the detector is placed on the rotating frame opposing the source (third generation CT scanner). The detector may comprise a single row of detector elements (single slice CT scanner), multiple rows of detector elements (multi-slice CT scanner) or area detector (cone beam CT scanner).

Scanner 26 may be operating in any of several scan modes known in the art: cone beam mode (a whole volume is scanned while the item holder is still), step and shoot mode (slabs of volume are scanned one at a time and the item holder is incremented from slab to slab) or spiral mode (the item holder is moving linearly while the scanner performs multiple rotations about it). Optionally, the item holder is rotated inside the scan volume while the radiation source and detector remain in place. The item holder preferably moves slowly so as not to move the items within it, for example, the item holder can rotate by 180° in 30 sec.

The inventor has found that a multiple slice X-ray scanner operating in spiral mode at 140 kVp generator voltage, beam current 30 mAs per slice or above, slice thickness of 1 mm and spatial resolution of 10 lp/cm gives good results for a bag filled with grocery items such as shown in FIG. 2A. However other scan parameters can be used, for example higher or lower generator voltage. In exemplary embodiments the design of the CT scanner and the scan parameters are adjusted according to the items to be identified and the tags attached to said items.

In some embodiments of the invention the transmitted radiation can be Gamma rays or any other type of radiation penetrating through the items. Different types of radiation can be used during the same scan operation, simultaneously or sequentially.

Optionally, the conveyer belt 30 that is used to load the item holder into the scanning volume 27 is used also to increment the item holder or move it continuously in step and shoot and spiral scan mode, respectively. Optionally the conveyer belt will load the item holder and a different conveyer belt that has characteristics that will improve scan quality (as lower attenuation which will cause fewer artifacts or greater precision movement) will increment the item holder in step and shoot and spiral scan mode. Optionally, the CT scanner has more than one X-ray source and/or more than one detector.

A controller 33 analyses the detected radiation to deduce the attenuation coefficients of voxels of the contents in volume 27. Controller as referred herein refers to a single controller that does the different control and computation tasks or a system of several controllers each assigned to some of the control and computation tasks.

The controller reconstructs a 3D image of the content of volume 27, showing the different materials (and items) in item holder 27. Any of the well known algorithms for such reconstruction can be used, for example filtered back-projection.

FIG. 2B shows a 3-D image of a box (not seen in the image due to low material density) filled with grocery items 22. Square and round tags 35 marked by hole patterns are attached to the items. In exemplary embodiment such as shown in FIG. 2B, the tags are composed of plastic plates, approximately 20 mm×20 mm in area and about 2 mm thick. The information is, for example, encoded as array of holes (or filled spaces) 2 mm in diameter at pitch 4 mm (see, for example, FIGS. 5A and 5B). Delrin plastic material with density approximately 1.4 provides a good differentiation in CT number (density) from most items found in a grocery. However, other tag dimensions, encoding scheme and compositions can be used.

In some embodiments of the invention, the information tags in the item holder can be identified in the reconstructed 3D image. Optionally, the 3D image only shows the location and the information on the tag is analyzed using other reconstruction means. Optionally, such other reconstruction means comprises a 2D image of the plane on which the tag is located. Alternatively, pattern recognition in the 3D data space is used.

Optionally, the 3D image is at a relatively low resolution which is enough to identify the location and, optionally, the orientation of the information tags. This allows for fast reconstruction of the scanning volume. In some embodiments, a 2D image of the plane on which the tag is located is reconstructed at a higher resolution. Optionally, after performing the CT scan and filtering the detected data, the whole volume of the item holder is first reconstructed at low resolution (big voxels) and then the filtered data is back-projected again only at a volume around the area of the tag, for a limited set of to voxels at high resolution (small voxels). In some embodiments the scan itself is repeated for the higher resolution image.

Optionally, when the location of the information on the tag is known, only these voxels are analyzed to read the information on the tag. For example, if the information on the tag is provided as different filings of holes in the tag, only the locations of the holes in the tag are analyzed to detect the material filling the holes.

Information on the items based on the information tags will be further detailed with reference to FIGS. 4, 5A and 5B which are schematic illustrations of information tags in accordance with exemplary embodiments of the invention.

In some embodiments of the invention, the information tag is adapted to be shown in the 3D image. The tag may be located in the 3D image by locating one or more of a material and a geometrical shape. Optionally, the geometrical shape comprises a pattern of and/or on the tag.

According to some embodiments of the invention, the tag comprises or is formed in a predefined geometrical shape which is not expected to be present in the items or item holder. For example, a tag 45 shown in FIG. 4 has the shape of a flower. Also tags 55 and 65 in FIGS. 5A and 5B have unique shapes. Tag 55 has a rectangular shape with a specific engraving or hole 39, tag 65 has a rectangular shape with a cut corner 64. These shapes and configurations are only exemplary.

Preferably, the predefined shape should be a non-uniform shape such that it has a low risk of being continuous with another tag. For example, hole 39 in tag 55 is depicted as two engravings, the first one is a hole 51 and the second one is a cylinder 53. Hole 51 and cylinder 53 are separated by a cylinder 52 which is made of the material of the tag or of a different material. The specific shape of hole 39 provides different discontinuities of the material of the tag, specifically, any plane that crosses the middle of the tag will show six different materials on a relatively small surface area. (tag 55, cylinder 53, cylinder 52, hole 51, cylinder 52, cylinder 53 and again tag 55). It is noted that hole 39 can be an engraving in the tag or a through hole, whereby cylinder 52 will be glued into the hole or engraving.

Optionally, different tags have different predefined shapes. For example, as shown in FIG. 2B, tags 35 have rectangular and round shapes.

In some embodiments, the tags have a shape (or shapes) which have a thickness such that the tags are locatable in a 3D image. Optionally, the thickness of a tag is about 1 mm, 2 mm, 3 mm or any intervening thickness.

Optionally, the predefined shape is made from one or more materials which have an attenuation coefficient different from the materials in the item to which it is associated. This will ease differentiation between the tag and the material it is attached to.

Following is an example where the items are water or oil in glass bottles. The Houndsfield number (HU) for water is 0, oil is about −100 and glass bottles have a Houndsfield number around 1200. By Hounsfield number (HU) is meant the density of the items in the CT image in units known in the art of medical CT imaging. Therefore, any material which has a different Houndsfield number than the above can be used. Examples of such materials are PVC (HU=~300) or Delrin (HU=~400). In addition, a mix of plastic and silicon can be created to provide the required value. Since plastic has a low HU value and silicon has a relatively high HU value, a mixture of these materials in proper proportions can provide a tag with almost any Houndsfield number between about −300 and about 1200. Other high Z materials, such as various metals can be mixed, in finely powdered form, with the low attenuation plastics. Care should be taken that the mixture is homogenous such that the different materials in the mixture will not show in the 3D image.

Optionally the tag will have a unique combination of materials and shapes. For example, a tag may be made of different materials, for example different layers of materials, wherein the combination of the materials is not expected to be found in any of the items in the item holder. Alternatively or additionally, the combination of the shape of the tag with the material from which the tag is made of is unique in that it is not expected to be found in any of the items in the item holder.

In some exemplary embodiments of the invention, the attenuation coefficient of the material from which the tag is made is known by the controller and assists in locating the tag. It is noted that forming a predefined shape by a material which is known provides yet an additional characteristic for locating the tag. For example, in order to overcome situations in which the items or item holder includes the material from which the tag is made or when two tags are positioned close to each other. In such situations, it may require a complex image recognition algorithm to differentiate between the tags and it is easier to identify the tags according to a combination of a predefined shape and material.

Optionally, different tags are made of different materials and the material is defined according to the item the tag is associated with. Optionally, tags having the same geometrical shape are also made from the same material. Accordingly, the shape can be located according to identification of a specific material. Optionally, a tag may be made of more than one material and the multiple materials assist in locating the tag.

In some embodiments of the invention the tag is made of any material and the CT number of the tag's material might not be used at all in location of the tag within the scan volume. In such embodiments the location is based on the shape of the tag and/or embedded pattern only.

According to some embodiments, the tag comprises a unique material which is not expected to be present in any of the items or the item holder. Thus, the unique material will have a different CT number than the materials in the items and will be easily identified by setting thresholds over the CT image. The tag(s) can be located, for example, by windowing the image.

In some embodiments of the invention the tag is made of a plurality of predefined materials, optionally including a unique material. For example, by different layers of materials, wherein optionally at least one of the layers includes the unique material. The tag may then be identified by thresholding the 3D image for the different materials and searching for proximity of the materials to each other. This is another characteristic that can be used in order to overcome cases where, although the unique material was not expected to be present in the items, one of the items does appear to include the unique material. The possibility of an item to include the layers of materials in proximity with another predefined material is generally low. In some embodiments, none of the layers is made of a unique material, and the tag is identified by the layers as the probability of having the layering of the tag in the items is low.

In some embodiments of the invention, the tag is made from a material that does not completely block radiation. This is desirable in order to ensure that the tag will not block the radiation used in the CT scan and will not disturb the reconstruction of the 3D image.

In some embodiments of the invention the tag comprises low density material such as a plastic sheet and has a small piece, such as a bit or several bits, of high density material such as steel bits embedded in it. Small enough bits do not introduce artifacts in the CT image. The bits are very easy to locate in the scan volume because there are no other isolated items of small size and high density. The bits can also be used to determine the orientation of the tag. A bit as referred herein relates to a small piece of material.

The 3D image is analyzed to locate the position of the tags in the image. Optionally, the predefined shape also provides information on the orientation of the item in the item holder. For example, hole 39 in tag 55 shown in FIG. 5 is located in the bottom right corner of the tag and can assist in orienting the tag. In addition, hole 39 can be an engraving only, and will enable differentiation between the front and rear surfaces of the tag. Alternatively, the unique material may be provided on a tag made of a different material and form a shape of for example three dots, or preferably, three filled holes, which are enough to identify a plane. Also cut corner 64 in tag 65 can determine the orientation of the tag.

Tags 25 may include or code information on the items. For example, a tag 25 may include or code information such as: name, type, manufacturer, manufacturing or expiry date, origin, price, materials and more. The code optionally does not contain any information itself, but refers to a listing of codes for information. The information may be presented by way of information of a code pattern 36 as shown in FIG. 4. Preferably, code pattern should have a minimum thickness. This can be provided by providing channels in the surface of the tag. These can be filled with a material with a different attenuation coefficient from the rest of the tag. Alternatively, the channels are filled and the difference in attenuation coefficient between air and the tag material provides enough x-ray contrast to read the code.

Alternatively or additionally, the information may be marked as a series of holes 37 as shown in FIGS. 5A and 5B. Optionally, holes 37 are arranged in a template of multiple holes (for example 40 holes on an 8×5 grid) which represent the same amount of information used with one of the Barcode standards. Optionally, a blank template tag is provided wherein the material in each of the holes is held by a thin material so that the hole can be easily punched out one at a time or several at one time or by removing like holes in a stack of tags, for example, using a punch in order to generate coded tags with specific code. The holes may, for example, represent a 1 bit in a barcode and when filled represent a 0 bit in a barcode. Optionally, the holes also form different shapes, such as rectangular, circle or triangle. The different shapes of the holes can provide different encodings, such that fewer holes are required in the tag. For example, if a hole can have the form of one of three shapes, each hole can represent a 0, 1, 2 or 3 value and 10 holes can represent a 40 bit number. Other types of information presentation may be used in as long as the controller is programmed to decode the information.

Optionally, the holes or engravings on the tag have different depths, such that the information on the tag can be read from a 3D image only.

Preferably the material of which the information code is formed contrasts (in the CT image) with the base material of the tag in order to provide clear showing thereof in the 3D (or 2D) image. Optionally, the material of the information code is air. Optionally, the material of the information code is metal bits embedded in the tags. Optionally a combination of more than two materials is used to encode more information in a given area. For example, a pattern of air holes, low density polymer, high density polymer and metal can encode values of 0, 1, 2 and 3 in one unit of information. Optionally, the information also comprises a depth which will ease the reading thereof from the 3D image.

For example, tag 65 shown in FIG. 5B has an array of holes 62 punched or drilled or formed by injection molding or any other manufacturing technique. Tag 65 is shown having 8 holes in array of 2×4 holes, as an example. However, other numbers of holes in other arrangement can be used. For example, hole diameters of 2 mm, center to center pitch of 4 mm and tag thickness of 2 mm can be used. Tag 65 may be made for example from Delrin with a CT number around 1.4. Other material can be used as well, as described above. The hole pattern can be used to encode numbers between 0 and 255, for example. In such a case, it can be determined that hole 66 near the cut corner signifies the least significant bit and hole 68 furthest from the cut corner signifies the most significant bits. A larger number of holes can be used to encode a larger span of numbers. Different holes can be assigned to encode different information.

Optionally, the information on the tag also includes an error correction bit or bits for correcting an error in reading the tag information. Alternatively or additionally, the information on the tag may include other error detection mechanisms, for example to verify correctness of the encoded information.

In some exemplary embodiments, the coded information on the tag can also assist in locating the tag and may form part of the located predefined geometrical shape.

Controller 33 may output a list with all or part of the information presented on the tags or images of the tags or represented by the code on the tags. Optionally, the controller provides a summary of the items, for example including the total price or weight of the items. Optionally, volume 27 also comprises a scale for weighing the item holder. The scale is preferably not in the radiated area so as not to interfere with the CT scan. Accordingly, the items will be weighed before or after the CT scan. The controller may calculate the actual weight of all the items and compare it with the expected weight, for example based on the information on the tags or based on information input to the controller by other means.

Alternatively or additionally, the controller may compare the volume of the different materials from the CT generated image with the expected volume of the items. Optionally, the controller compares volumes of a specific CT number, thereby checking the volume of a specific material with their expected volume. Optionally, the controller compares the volume of a plurality of CT numbers, thereby checking the volume of a plurality of specific materials with their expected volume. The expected volume is optionally obtained from the information tags or in combination with other sources, such as databases stored in the controller.

The controller may then output an indication of the accuracy of the scan, based on the compared weight or volume.

In addition, the controller may check if one or more of the tags are attached to their intended item. For example, the controller may check for fraud when a tag of a low cost item is put on a more expensive item. In this case, the controller will analyze the shape and/or CT number of the item itself and compare this information with the information on the tag of the item or in the list of items provided by the controller. For example, when the tag is intended for a bottle but is attached to a rectangular box. Optionally, the shape of an item is not easy detected from the reconstructed CT image and the CT number of the item is also checked.

Optionally, this check is randomly performed. Alternatively, the controller receives information on common stolen items and only these items are checked. Recognition of the shape of the items is performed according to any of the known image recognition algorithms. Optionally, the controller will generate a warning when such a comparison results negative, i.e. when fraud is detected. Alternatively, the controller may send a signal to an outside source, such as to the manager of a grocery store, when fraud is detected.

Optionally, the tags are fixed to the items. Alternatively, the tags are embedded in the items or part of the item's package. Alternatively, the tags are injected or molded in the items or their package. Alternatively, the tags are inserted in the items. In some embodiments of the invention, some tags are inserted in the item holder, without the item it is associated with. For example, when the item is too big to be inserted in the item holder or for contributing to charity. Alternatively, some tags do not have an associated item but provide general information, such as the identity of the buyer or a gift card.

In some embodiments of the invention, controller 33 further analyses the image to provide additional information, such as for example, to locate items which have no tags, or items with double tags. This is performed for example by analyzing a contour of an item or a CT number of an item and checking if more than one tag is located on said contour, or if no tag is positioned thereon.

Optionally, this analysis is only performed when the weight or volume of the items does not match the expected weight or volume, as described above. The controller may receive input information on the item holder or the type of items or the price of the items. Alternatively or additionally, the controller may receive information which is not directly related to the items, for example, information on a "happy hour" in a supermarket where all the items enjoy a 50% reduction in price.

Figure 6:
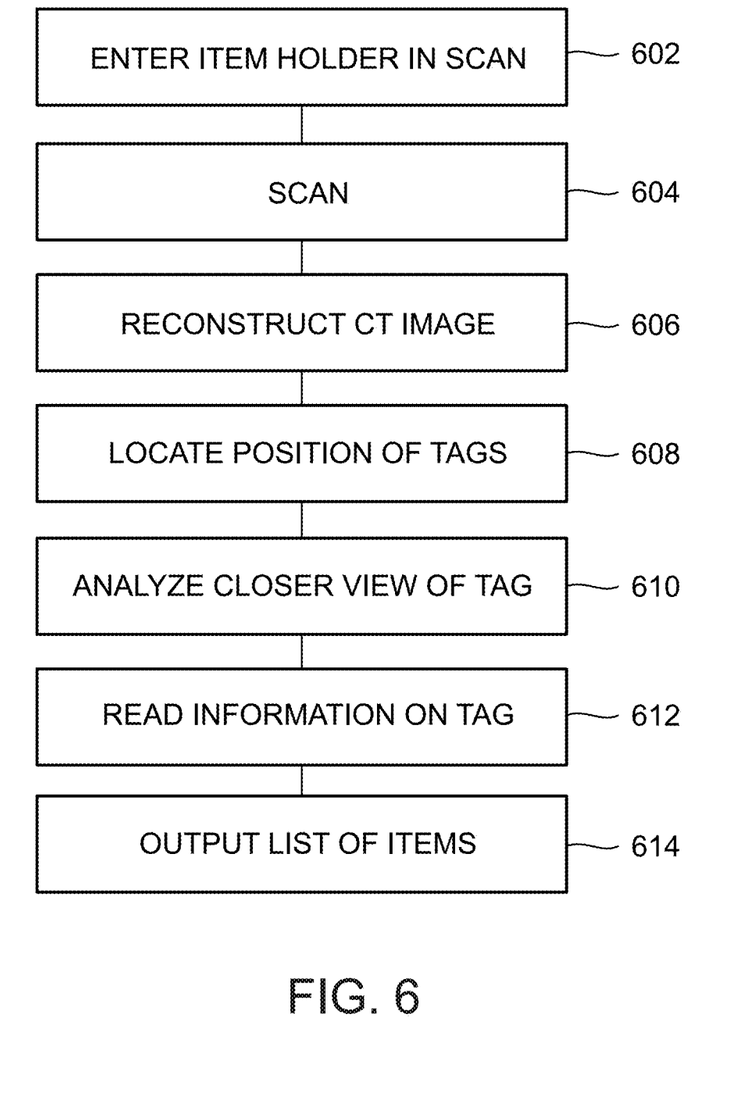
FIG. 6 is a flowchart of a method of identifying unorganized items in accordance with some embodiments of the invention.

FIG. 6 is a flowchart of a method 600 of identifying unorganized items in accordance with some embodiments of the invention. An item holder including a plurality of unorganized items is entered into a CT scanner at 602. The item holder may be any item holder of dimensions compatible with the scan holder and composition suitable for undergoing a CT scan, for example as shown in FIG. 1 or 2.

At 604 a CT scan of the item holder is performed, for example with the CT scanner 300 shown in FIG. 3. Optionally, if an algorithm or operator detects that the detected signals are too low the scan is repeated. Preferably, the repeated scan is with different parameters, for example with higher radiation intensity or higher X ray energy or longer acquisition time. Optionally, the repetition of the scan is performed automatically. Alternatively or additionally, the controller only warns of such excessive noise and the operator performs the scan again.

A 3D image of the item holder is then reconstructed at 606. Reconstruction of a 3D image from a CT scan is well known in the art and any known method therefore can be used in accordance with some embodiments of the invention. Optionally if an operator or an algorithm detects excessive image noise the scan is repeated. Preferably, the repeated scan is with different parameters, for example with higher radiation intensity or higher X ray energy or longer acquisition time. Optionally, the repetition of the scan is performed automatically. Alternatively or additionally, the controller only warns of such excessive noise and the operator performs the scan again.

The position of information tags is located at 608 from the 3D image. Optionally, the position is located based on a unique material or other predefined material(s) provided in the tags, as explained with reference to FIGS. 4 and 5 above. Alternatively or additionally, the location is based on a predefined shape and/or depth of the tags. Alternatively or additionally, the location is based on a pattern embedded in the tags. Alternatively or additionally, the location is based on a bit or bits of high density material embedded in the tags.

Optionally, the location of the tag in the image is found using a shape recognition algorithm such as for example a convex hull algorithm which results in a construction of the 3D (or 2D in some cases) item including the material of the tag. The controller will search for points in the 3D image of the material from which the tag is made. Optionally, points of materials having a Houndsfield number close to the Houndsfield number of the tag material will also be analyzed. The controller then searches for continuous points using the same material (or close material) and results a 3D image of the largest convex of materials found. Any of the well known convex hull algorithms may be used for said purpose.

Optionally the entire scan volume is segmented to sub-volumes of approximately the same CT number. Tags are then identified by CT number profile and/or shape.

Optionally, if an operator or an algorithm detects image artifacts that may temper the readout of tags information a warning is generated.

Preferably, the controller will then verify that the 3D shape found is indeed a tag. The controller verifies if the shape found is identical to an expected tag shape. The controller may save in its memory all possible shapes of a tag in the item holder. Optionally, the controller is aware of which shape is made of which material such that not all materials have to be compared with each of the possible tag shapes.

After locating the information tag in the image, a closer view of said location is analyzed at 610. Optionally, said closer view comprises a 2D image of a plane on which the tag is positioned. Alternatively, the closer view is a 3D image of the tag itself, as received by the convex hull algorithm. Alternatively or additionally, such closer view comprises a view of the location (voxels) where the information on the tag is located.

The information on the tag is read from the closer view at 612. Any of the well known image processing algorithms may be used for said purpose. Optionally the image processing algorithms include any of noise filtering, edge enhancement, multi-planar reformatting, curved multi-planar reformatting, minimum intensity projection, maximum intensity projection. Optionally the image processing algorithms include comparison of sub-images out of the scan image with images from a library.

In some embodiments of the invention, the information is derived by determining the CT number at those parts of the tag which may contain particular materials, holes or the like. This allows for interrogating only a limited number of positions on the tag.

After identifying all the items in the item holder, a list of all items and/or other information is produced at 614. The list may include information on each item or only a total of the items. Optionally, the list includes information received from the tag and also other information, received from other sources that might relate directly to the tag information or indirectly. For example, the information may include prices of the items, special reductions (either general or on particular items), commercials and/or information on the buyer of the items. Optionally, the list also includes remarks such as the presence of items without a tag, tags without items or the accuracy of the scan performed.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of identifying a plurality of items, the method comprising:
   performing a CT scan of a plurality of items in an unorganized pile, at least some of said items bearing information tags;
   reconstructing an image based on the CT scan; and
   identifying a plurality of information tags associated with the items based on the reconstructed image.

2. A method according to claim 1, wherein the tag comprises an identifiable material and wherein identifying the tag comprises identifying said material.

3. A method according to claim 1, wherein identifying an information tag comprises identifying a plurality of materials, where at least one tag comprises different materials and where at least two different tags comprise different sets of materials.

4. A method according to claim 1, wherein identifying an information tag comprises identifying pieces of high attenuation material on or in the tags.

5. A method according to claim 1, wherein identifying an information tags comprises identifying a predefined geometrical shape of the tags.

6. A method according to claim 5 wherein identifying an information tag comprises identifying by a shape recognition algorithm.

7. A method according to claim 1 wherein identifying an information tag comprises identifying a pattern on the tag.

8. A method according to claim 7 wherein identifying an information tag comprises identifying by a pattern recognition algorithm.

9. A method according to claim 1, wherein identifying an information tag comprises identifying a combination of any of materials and geometrical shapes of the tag.

10. A method according to claim 1, wherein the method further comprises reading information related to the item from the information tag.

11. A method according to claim 10, wherein reading information comprises reading a pattern embedded in the tag.

12. A method according to claim 10, wherein reading information comprises identifying bits embedded in the tag.

13. A method according to claim 10, wherein reading information comprises identifying grooves or holes in the tag.

14. A method according to claim 13, wherein identifying grooves or holes comprises identifying a CT number of a material filling the grooves or holes.

15. A method according to claim 10, the method further comprising:
   determining CT numbers associated with an item;
   analyzing a shape and the CT numbers of the item; and
   comparing said shape and/or CT numbers with the information derived from the tag.

16. A method according to claim 15, the method further comprising:
   generating a warning when said comparison is negative.

17. A method according to claim 1, wherein identifying an information tag based on the reconstructed image comprises:
   identifying a plane on which the information tag is positioned based on the reconstructed image;
   reconstructing a 2-D image of the plane on which the tag is identified; and
   identifying the tag based on the 2-D image.

18. A method according to claim 1, wherein identifying an information tag based on the reconstructed image comprises reading information from the information tag from a 3D image.

19. A method according to claim 18, wherein reading information from the information tag comprises analyzing only voxels in the image where information is expected to be located.

20. A method according to claim 1, wherein constructing an image based on the CT scan comprises constructing a first low resolution image of said items and constructing a second higher resolution image of the volume around the located tags.

21. A method according to claim 1, wherein the method further comprises providing an item holder containing said plurality of items.

22. A method according to claim 21, wherein providing an item holder comprises providing an item holder containing a plurality of information tags associated with the plurality of items and wherein performing a CT scan of a plurality of items comprises performing a CT scan of the plurality of tags.

23. A method according to claim 22, wherein providing an item holder containing a plurality of information tags comprises providing an item holder containing a plurality of information tags wherein at least one of the tags is associated with an item that is not in the item holder.

24. A method according to claim 22, wherein providing an item holder containing a plurality of information tags comprises providing an item holder containing a plurality of information tags wherein at least one of the tags is not associated with a particular item.

25. A method according to claim 21, wherein providing an item holder comprises providing an item holder made of a low attenuation coefficient material.

26. A method according to claim 1, the method further comprising:
   generating information on the items associated with the tags.

27. A method according to claim 26, the method further comprising:
   analyzing the outer surface of an item from the plurality of items; and checking if information on said item is provided in the generated information.

28. A method according to claim 1, wherein constructing an image based on the CT scan and identifying an information tag, further comprises one or more of noise filtering, edge enhancement, segmentation of the image to sub volumes of different densities, pattern recognition, multi-planar reconstruction and curved multi-planar reconstruction.

29. A method according to claim 1, the method further comprising:
detecting that the reconstructed image is noisy and
performing an additional CT scan of the items.

30. A method according to claim 29, wherein performing an additional scan comprises performing an additional scan with different scan parameters than the first CT scan.

31. A method according to claim 1, the method further comprising:
detecting that the signals detected by the CT scan are low; and
performing an additional CT scan of the items.

32. A method according to claim 1, the method further comprising:
calculating a volume of the items from the reconstructed image;
comparing said calculated volume with the expected volume based on information derived from the information tags.

33. A method according to claim 32, wherein calculating a volume of the items comprises calculating a total volume of approximately a same CT number in the items.

34. A method according to claim 1, the method further comprising:
generating a warning if any of the items generates image artifacts or if the tags might be tampered with.

35. A method according to claim 1, wherein performing a CT scan of a plurality of items comprises performing a CT scan of a plurality of grocery items.

36. A method according to claim 1, further comprising:
placing items in an item holder, said item holder being one of a box, bag, luggage, basket, package or shopping cart, at least some of said items bearing an information tag that can be distinguished in an image based on a CT scan.

37. A method according to claim 36, wherein the tag comprises an identifiable material and wherein identifying the tag comprises identifying said material.

38. A method according to claim 36, wherein identifying an information tags comprises identifying a predefined geometrical shape of the tags.

39. A method according to claim 36, wherein identifying an information tag comprises identifying a combination of any of materials and geometrical shapes of the tag.

40. A method according to claim 36, wherein the method further comprises reading information related to the item from the information tag.

41. A method according to claim 40, wherein reading information comprises identifying grooves or holes in the tag.

42. A method according to claim 40, the method further comprising:
determining CT numbers associated with an item;
analyzing a shape and the CT numbers of the item; and
comparing said shape and/or CT numbers with the information derived from the tag.

43. A system for identifying a plurality of items, the system comprising:
a CT scanner operable to scan a plurality of items in an unorganized pile, the items comprising a plurality of tags including information for said items;
an image reconstructor adapted to reconstruct an image of said items; and
a controller adapted to locate the tags within said image and read the information on the tags from said image.

44. A system according to claim 43, wherein the controller is further adapted to generate a warning when an item of the plurality of items generates image artifacts.

45. A system according to claim 43, wherein the controller is further adapted to instruct rescanning of the items with different parameters when low signals are detected during the scan.

46. A system according to claim 43 wherein the controller is further adapted to instruct rescanning of the items with different parameters when the quality of the reconstructed image is insufficient for locating the tags.

47. A system according to claim 43, wherein the controller is further adapted to compare the volume of the items in the reconstructed image with an expected volume of the items as derived from the information on the tags.

48. A system according to claim 47, wherein the compared volume is a volume of approximately a same CT number in the reconstructed image.

49. A system according to claim 47 wherein the controller is further adapted to generate a warning when the expected volume of the different materials is different than the volume derived from the information on the tags.

50. A system according to claim 43, wherein the CT scan is operable to scan tags without their associated items.

51. A system according to claim 43, wherein the system further includes a scale for weighing the items and the controller is further adapted to compare the weight of the items with an expected weight of the items as derived from the information on the tags.

52. A system according to claim 43, wherein the controller is further adapted for:
determining CT numbers associated with an item;
analyzing the shape and CT numbers of the item; and
comparing said shape and/or CT numbers with the information derived from the tag.

53. A method according to claim 36, the method further comprising:
calculating a volume of the items from the reconstructed image;
comparing said calculated volume with the expected volume based on information derived from the information tags.

54. A system according to claim 43, wherein said plurality of items are placed in an item holder, the item holder being one of a box, bag, luggage, basket, package or shopping cart.

55. A system according to claim 54, wherein the controller is further adapted for:
determining CT numbers associated with an item;
analyzing the shape and CT numbers of the item; and
comparing said shape and/or CT numbers with the information derived from the tag.

* * * * *